US006332088B1

United States Patent
Zhang et al.

(10) Patent No.: US 6,332,088 B1
(45) Date of Patent: Dec. 18, 2001

(54) METHOD AND APPARATUS FOR IMAGING INSTRUMENTS DURING INTERVENTIONAL MRI USING ASYMMETRIC SPIN ECHO SEQUENCES

(75) Inventors: Weigno Zhang, Foster City; Leon Kaufman, San Francisco; Hector Avram, Foster City, all of CA (US)

(73) Assignee: Toshiba America MRI, Inc., Tustin, CA (US)

( * ) Notice: Subject to any disclaimer, the term of this patent is extended or adjusted under 35 U.S.C. 154(b) by 0 days.

(21) Appl. No.: 09/190,599

(22) Filed: Nov. 12, 1998

(51) Int. Cl.[7] .................................................. A61B 5/05
(52) U.S. Cl. .................. 600/410; 324/307; 324/309; 324/310; 324/311; 324/312; 324/314; 324/318
(58) Field of Search ...................... 600/407, 410; 324/307, 309, 310, 311, 312, 314, 318, 300; 128/653

(56) References Cited

U.S. PATENT DOCUMENTS

| | | | |
|---|---|---|---|
| 4,703,268 | * 10/1987 | Gyngell et al. | 324/309 |
| 4,720,679 | * 1/1988 | Patrick et al. | 324/309 |
| 4,788,500 | * 11/1988 | Patz et al. | 324/309 |
| 4,837,513 | 6/1989 | Yao . | |
| 4,986,272 | 1/1991 | Riederer et al. . | |
| 5,168,227 | * 12/1992 | Foo et al. | 324/309 |
| 5,202,631 | 4/1993 | Harms et al. . | |
| 5,214,382 | 5/1993 | Harms et al. . | |
| 5,218,964 | 6/1993 | Sepponen . | |
| 5,245,282 | * 9/1993 | Mugler, III et al. | 324/309 |
| 5,280,245 | 1/1994 | Pauly . | |
| 5,296,809 | 3/1994 | Roberts et al. . | |
| 5,446,384 | 8/1995 | Dumoulin . | |
| 5,459,401 | * 10/1995 | Kiefer | 324/309 |

OTHER PUBLICATIONS

Stables, Lara A. et al., "Asymmetric Spin–Echo Imaging of Magnetically Inhomogeneous . . . ", MRM 40, 1998, pp. 432–442.

* cited by examiner

Primary Examiner—Marvin M. Lateef
Assistant Examiner—Jeoyuh Lin
(74) Attorney, Agent, or Firm—Nixon & Vanderhye P.C.

(57) ABSTRACT

An asymmetric spin-echo (ASE) sequence having a variable asymmetry ($\Delta TE$) with respect to the RF pulse is used for imaging paramagnetic, diamagnetic or ferromagnetic instruments within tissues during interventional MRI procedures. The degree of asymmetry introduced determines an apparent size of the imaged instrument. In one embodiment of the invention, the amount of asymmetry is varied as a function of the phase encoding gradient steps. In this manner, the sequence is made sensitive to local gradients in the magnetic field but left insensitive to large scale variations such as those introduced by main magnetic field inhomogeneities.

11 Claims, 4 Drawing Sheets

METHOD AND APPARATUS FOR IMAGING INSTRUMENTS DURING INTERVENTIONAL MRI USING ASYMMETRIC SPIN ECHO SEQUENCES

FIELD OF THE INVENTION

This invention relates generally to interventional magnetic resonance imaging (IMRI) techniques. In particular, it relates to methods and apparatus for the imaging of paramagnetic, diamagnetic or ferromagnetic instruments within tissues during interventional procedures and, more particularly, to a method of generating of an asymmetric spin-echo imaging sequence whereby the apparent size of such an instrument can be varied.

BACKGROUND OF THE INVENTION

Magnetic Resonance Imaging (MRI) has become a widely accepted and commercially available technique for obtaining digitized visual images representing the internal structure of objects (such as the human body) having substantial populations of atomic nuclei that are susceptible to nuclear magnetic resonance (NMR) phenomena. In MRI, nuclei in a body to be imaged are polarized by imposing a strong main magnetic field Ho on the nuclei. Selected nuclei are excited by imposing a radio frequency (RF) signal at a particular NMR frequency. By spatially distributing the localized magnetic fields, and then suitably analyzing the resulting RF responses from the nuclei, a map or image of relative NMR responses as a function of the location of the nuclei can be determined. Following a Fourier analysis, data representing the NMR responses in space can be displayed on a CRT.

Figure 1:
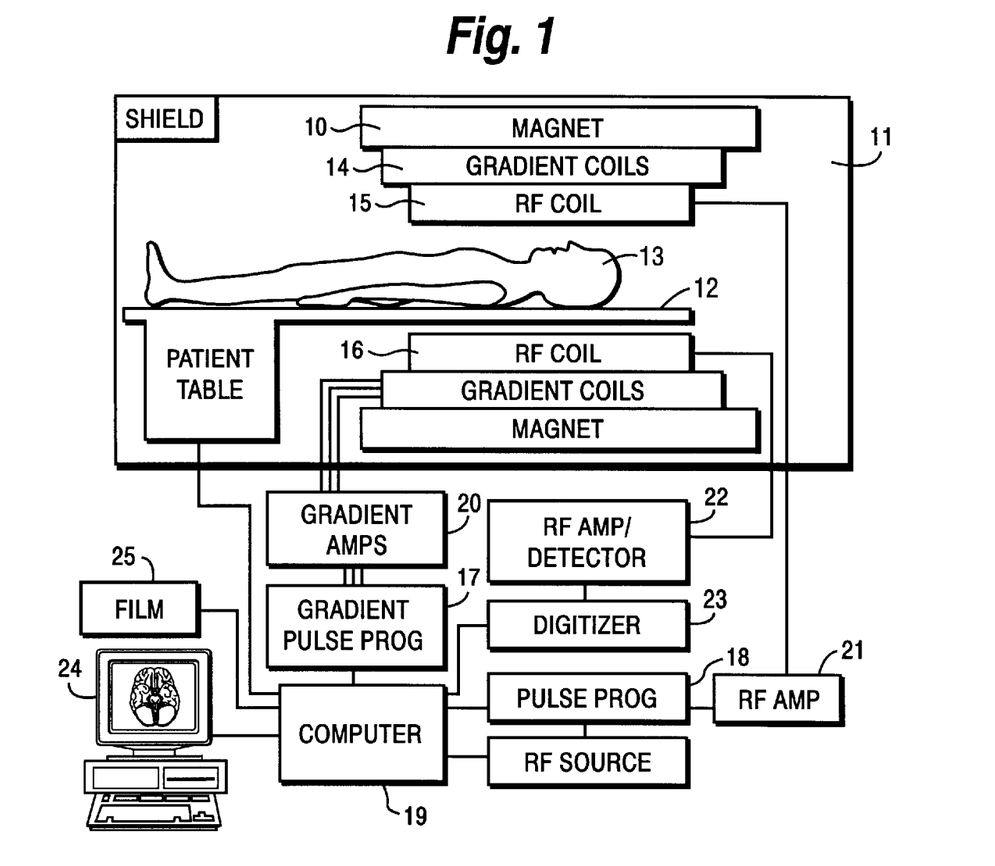
FIG. 1 is a schematic diagram of an example MRI system.

As shown in FIG. 1, the NMR imaging system typically includes a magnet 10 to impose the static magnetic field, gradient coils 14 for imposing spatially distributed magnetic fields along three orthogonal coordinates, and RF coils 15 and 16 to transmit and receive RF signals to and from the selected nuclei. The NMR signal received by the coil 16 is transmitted to a computer 19 which processes the data into an image displayed on display 24. The magnetic resonance image is composed of picture elements called "pixels." The intensity of a pixel is proportional to the NMR signal intensity of the contents of a corresponding volume element or "voxel" of the object being imaged. The computer 19 also controls the operation of RF coils 15 and gradient coils 14 through the RF amplifier/detector 22 and gradient amplifiers 20, respectively.

Each voxel of an image of the human body contains information representative of one or more tissues. The tissues of the human body are comprised primarily of fat and water. Fat and water have many hydrogen atoms (the human body is approximately 63% hydrogen atoms). Since hydrogen nuclei have a readily discernible NMR signal, magnetic resonance imaging of the human body primarily images the NMR signal from the hydrogen nuclei.

Basically, in NMR a strong static magnetic field is employed to commonly align atoms whose nuclei have a spin angular momentum and a magnetic dipole movement, i.e., atoms whose nuclei have an odd number of protons and/or neutrons. A second magnetic field, applied transverse to the first field as a single RF pulse, pumps energy into the nuclei, which causes the angular orientation of the nuclei to flip by, for example, 90° or 180°. After this excitation, the nuclei precess and gradually relax back into alignment with the static field. As the nuclei precess and relax, they will induce a weak but detectable electrical energy in the surrounding coils that is known as free induction decay (FID). These FID signals, as well as magnetic gradient or RF refocused "echoes" thereof, which are collectively referred to herein as MR signals, are analyzed by a computer to produce images of fat and water containing tissue; of the body.

The excitation frequency and the FID frequency are related by the Larmor relationship. This relationship states that the angular frequency, $\omega_0$, of the precession of the nuclei is the product of the magnetic field, $B_0$, and the so-called magnetogyric ratio, $\gamma$, a fundamental physical constant for each nuclear species:

$$\omega_0 = B_0 \cdot \gamma$$

By superimposing a linear gradient magnetic field, $B_z = Z \cdot G_z$ on the static uniform field, $B_0$, which is typically defined as the Z axis, for example, nuclei in a selected X-Y plane may be excited by proper choice of the frequency of the transverse RF excitation field pulse applied along the X or Y axis. In addition, gradient magnetic fields are applied in the X-Y plane during detection of the MR signals to spatially localize emitted MR signals from the selected X-Y plane according to their frequency and phases.

As mentioned above, the main magnetic field can be altered by gradient magnetic fields created in the X, Y, and Z directions of the imaging volume. For the purpose of simplifying the descriptive mathematics, a rotating reference coordinate system X'-Y'- Z', that rotates at the nominal Larmor frequency about the Z' axis, is often used to describe nuclear phenomenon in NMR. Selected nuclei, which precess in alignment with the $B_0$ field, are influenced (nutated) by the perpendicular magnetic field of an RF pulse at the Lamor frequency, causing a population of such nuclei to tip from the direction of the magnetic field $B_0$. Thus, certain nuclei start aligned with the "Z'" axis by the static $B_0$ field and then are rotated to the X'-Y' plane as a result of the RF signal pulse being imposed on them. The nuclei then precess about the Z' axis in the X'-Y' plane.

The RF nutating pulse will, of course, tip more than one species of the target isotope in a particular area. For the purpose of simplifying the description and analysis of an MRI acquisition sequence, each RF pulse used in the sequence is characterized by its center—which is representative of the time at which the nutated precessing nuclei can be considered as all being in-phase (synchronized) and after which each species of nuclei will begin to precess at their own characteristic speed. The phase of the precessing nuclei species will gradually differ (de-phase) as a result of such parameters as the physical or chemical environment in which the nuclei are located.

Once the magnetic moments of the nuclei are disturbed from their equilibrium, processes known as "relaxation" causes the Z'-component of the spinning (precessing) magnetic moments to recover to an equilibrium magnitude, $M_0$, in alignment with the background $B_0$ field, and the phase-coherent component in the X'-Y' plane to decay. The duration of these relaxation processes are termed the "spin-lattice relaxation" time and the "spin-spin relaxation" time and are characterized by exponentials whose defined time constants are labeled as $T_1$ and $T_2$, respectively. As magnetic resonance signals are exhibited through the oscillation of magnetic flux from nuclei in a plane coexistent with the X'-Y' plane, both of these relaxation processes cause the signal strength to decrease as a function of time. In the interests of accuracy, an "apparent relaxation" time constant, $T_2^*$, is often defined as characterizing transverse signal decay due to spin-spin relaxation in the presence of $B_0$ field inhomogeneities.

Figure 2:
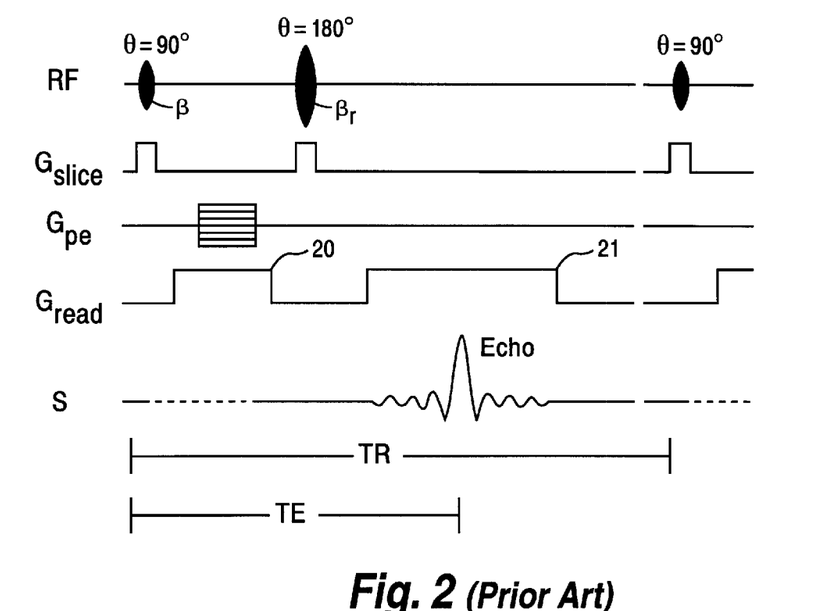
FIG. 2 is an RF and gradient waveform timing diagram of an example MRI pulse sequence for generating a spin-echo MRI response.

An operation whereby the various coils produces RF excitation pulses and gradient fields to result in an MR signal is called an MRI "acquisition sequence." A graphical representation of an example MRI acquisition sequence is shown in FIG. 2. In this example, the particular timing of applied RF pulses and magnetic fields is known as a "spin-echo" sequence since the MR signals appear as an "echo" of a 180° spin rotation RF pulse. First, a gradient field, $G_{slice}$, is superimposed along the main field to sensitize a "slice" or "slab" (for 3D imaging) of nuclei in the patient's body tissue to a particular RF resonance frequency. A 90° RF excitation or "nutation" pulse, β, is then applied at the particular frequency to force some of the nuclei within the slab to precess in a direction perpendicular with respect to the main field. Thereafter, pulsed magnetic gradient fields of changing magnitudes, $G_{pe}$ (and $G_{slice}$ for 3D imaging), are used to phase encode the nuclei by inducing a temporary frequency difference, and hence phase differences, between nuclei in different locations along a specific direction within the slab. At the same time, a dephasing magnetic gradient field pulse 20 is applied orthogonal to the direction of $G_{pe}$ (shown at $G_{read}$) to de-phase the precessing nuclei. Next, a "refocusing" RF pulse, $β_r$, causing a 180° rotation of the spinning (precessing) nuclei is applied followed by a "readout" (frequency encoding) magnetic field gradient 21 ($G_{read}$) applied orthogonal to phase encoding gradient $G_{pe}$. The 180° refocusing RF pulse causes the spinning magnetization directions of the nuclei to at least partially re-phase—which results in producing the "spin-echo" MR signal S.

In practice, MRI sequences are almost always arranged such that the pulsed magnetic field gradients will be completely balanced by the time the center of the induced MR signal occurs (i.e., the so called "echo-center"). This is accomplished by either reversing the read-out gradient one or more times to create "field-echoes" or by applying 180° spin rotation RF "refocusing" pulses to create "spin-echoes."

The time period from the center of the 90° nutating pulse to the center of the spin-echo MR signal is designated as TR, the "echo time", and the entire pulse sequence duration is designated as TR, the sequence "repetition rate." Conventionally, a spin-echo sequence is "symmetric" in that the period between the 180° RF pulse and the resultant echo signal is the same as the period between the 90° RF pulse and the 180° RF pulse.

Basically, the phase-encoding gradient field, $G_{pe}$, encodes nuclei in a selected slab or slice in a first direction and the applied read-out gradient field, $G_{read}$, frequency encodes the nuclei in the same slice in an orthogonal direction (also called the "readout direction"). An MR "echo" signal, S, resulting from the application of the read-out gradient field, is then acquired for many sequences, each having a unique phase encoding gradient value $G_{pe}$. The acquired data (also called "raw data" or "k-space data") is then analyzed by Fourier analysis. A scaled frequency domain plot of that analysis renders information about the nuclei population in Fourier space (also referred to as the image domain), which corresponds to an X-Y-Z position.

Interventional Magnetic Resonance Imaging

For certain interventional applications of MRI (IMRI) it is highly desirable to visualize the placement of a needle or catheter within tissues. Unfortunately, the visualization properties of these instruments are complex because they are typically paramagnetic. Distortions in the static and/or weakly ferromagetic gradient magnetic fields are introduced by this paramagnetism and are dependent on the strength of the main field and gradient field, and the orientation of the long axis of the needle or catheter with respect to the main and gradient fields. The distortions consequently observed in MR images also depend on whether spin-echo or gradient-echo imaging techniques are used. Typically, the image distortions of paramagnetic instruments are of two kinds: 1) an apparent magnification of the size of an intervening instrument and 2) an apparent shift in the position of the instrument with respect to surrounding tissues.

The increased apparent size of an intervening instrument is primarily due to shifts in resonance frequencies and magnetic field inhomogeneties. In two dimensional (2D) imaging, linear gradients are used together with frequency selective excitation pulses to define the position of a section of interest through the tissue. For a paramagnetic object—which in itself appears as a signal void—the spins of nuclei in tissues near the object are shifted in resonance frequency to a much different value and may completely miss the RF excitation. In addition, a paramagnetic object or instrument introduces large magnetic field inhomogeneities in its vicinity. This causes diffusion-related loss of signals. Moreover, for gradient recalled echo (GRE) or asymmetric spin-echo (ASE) signals—that is, signals with a mixture of both GRE and SE—there is an additional signal loss due to intra-voxel dephasing. All these effects can cumulatively increase the apparent size of a void area introduced into the image by the paramagnetic object.

In GRE imaging, the magnitude of the spin dephasing effect depends primarily on the echo time TE (defined as the time between the 90° excitation pulse and the maximum amplitude point of the echo signal). The longer the TE, the greater the dephasing effect. Unfortunately, shortening TE (for example, to alter the apparent size of a paramagnetic object) imposes extra requirements on gradient strength and RF power. Moreover, as TE gets shorter, the consequently shorter echoes suffer a decreased signal-to-noise ratio. In contrast, in a conventional symmetric spin-echo sequence (SE)—where the TE is always twice the time between the RF excitation pulse and the RF refocusing pulse—the above relationship between the duration of TE and intra-voxel dephasing is not utilized. However, if the spin-echo sequence is made asymmetric, the dephasing effect will then depend on the degree of asymmetry.

This dephasing effect of an asymmetric spin-echo sequence and its application to magnetic resonance imaging (MR) has also been addressed in *Asymmetric Spin-Echo Imaging of Magnetically Inhomogeneous Systems: Theory, Experiment, and Numerical Studies* by Stables et al., MRM (1998). In that article, Stables et al. describe ASE imaging sequences for visualizing magnetically inhomogeneous systems such as blood capillaries. For example, Stables et al. use theory and computer simulations to demonstrate that an ASE sequence can provide a form of "susceptibility relaxation" contrast in an image that is dependent on the size of the field perturbation present (e.g., the size of a capillary). However, the discussion therein is primarily directed toward using ASE echo-planar type imaging (EPI) sequences for producing Blood Oxygenated Level Dependent (BOLD) contrast effects and does not address problems arising in IMRI concerning the visualization and placement of imaged instruments.

For example, the placement of needles or catheters under MR fluoroscopy (i.e., real time MR imaging) often involves tradeoffs between image refresh time (t) and signal-difference-to-noise (SD/N) of the images. When a needle is being introduced, an operator may want short refresh times, but the short refresh times may compromise the S/N ratio, e.g., due to the lack of averaging (n) and/or phase encoding steps (P), and thus make the void introduced by the needle difficult to see in the resultant image. In this case, not only does the S/N ratio suffer, but if the needle is smaller than the voxel, contrast is reduced because of partial volume averaging due to larger voxels along the phase-encoding (PE) direction.

For the case where echo time (TE) and echo duration are constant, the signal-difference-too-noise ratio is a product of contrast (C) and S/N. If speed is achieved by reducing the number of phase encoding steps (P) for a fixed field of view, then C P if the apparent diameter of the needle is less than the relevant voxel dimension—i.e., $S/N (n/P)^{1/2+ee}$ and $SD/N (nP)^{+e,fra\ 1/2}$. Consequently, as faster scanning is achieved by reducing phase encoding steps P, needle conspicuity is reduced. In contrast, for the case where the apparent diameter of the needle is larger than the relevant voxel dimension, contrast C does not change when P changes and $SD/N (n/P)^{1/2}$. In this case, shortening refresh times by reducing the number of phase encoding steps P improves needle conspicuity.

Consequently, an object of the present invention is to exploit the above discussed dephasing phenomena to an advantage in IMRI procedures by utilizing an asymmetric spin-echo sequence and controlling the degree of asymmetry of the echo signal with respect to the RF excitation pulse to provide improved visualization and predictable control over the apparent size of an imaged instrument.

SUMMARY OF THE INVENTION

The present invention provides a new IMRI method and MRI scan sequence for use in imaging paramagnetic, diamagnetic or ferromagnetic instruments within tissues during interventional MRI procedures (e.g., to visualize the placement of a needle or catheter). Basically, the invention involves a method of generating an asymmetric spin-echo imaging (ASE) sequence whereby the apparent size of such an instrument can be varied in the resulting image. More specifically, an asymmetric spin-echo (ASE) sequence is used during an interventional MRI procedure. In accordance with the present invention, the degree of asymmetry introduced determines the apparent size of an imaged instrument. For example, using a large degree of asymmetry, a needle can be made to appear large during the initial stages of its introduction into the imaged tissue. Subsequently, when better localization is needed, as when the needle is near an intended target, its apparent size can be decreased by decreasing the amount of asymmetry.

In a second embodiment of the invention, the amount of asymmetry in the ASE sequence is varied as a function of the phase encoding gradient steps. In this manner, the sequence is made sensitive to local gradients in the magnetic field but left insensitive to large scale variations such as those introduced by main magnetic field inhomogeneities.

BRIEF DESCRIPTION OF THE DRAWINGS

The purpose and advantages gained by the present invention will be understood by careful study of the following detailed description of the presently preferred embodiment with particular reference to the accompanying drawings.

DETAILED DESCRIPTION OF THE PRESENTLY PREFERRED EMBODIMENT

As is well-known, nuclei precess at a particular frequency with a particular phase. By applying gradient fields to the nuclei in different orthogonal directions, the frequency and phase of the precessions can be used to spatially encode the nuclei. In one orthogonal direction, a "slice" of nuclei are excited. Within that slice, MR signals are extracted from the remaining two dimensions of the slice, using the frequency of precession of the selected nuclei to spatially encode the nuclei in one direction and using the phase of precession of the selected nuclei to spatially encode the nuclei in the second (or other) direction(s). By analyzing the complex signal magnitude and phase of the resultant MR signal, information about the nuclei density in the selected slice can be determined.

FIG. 1 depicts an MRI system. One example of such a system is the Toshiba OPART™ MRI system. Such an MRI system may comprise a large polarizing magnet structure 10 which generates a substantially uniform homogeneous polarizing magnetic field $B_0$ within a patient imaging volume 11. A suitable carriage 12 inserts the desired portion of patient 13 anatomy within the image volume 11. Magnetic gradients in $B_0$ are selectively created by electromagnetic gradient coils 14. RF nuclei nutation pulses are transmitted into the patient tissue within the image volume by RF coil 15. The RF responses constituting the MR signal are received from the patient tissue via suitable RF detection coil structures (RF/ADC) 16.

To acquire MRI data, the MRI system generates magnetic gradient and RF nutation pulses via MRI pulse sequence controllers 17 and 18 under the control of programmable computer/processor 19. In addition, processor 19 controls gradient pulse amplifier 20 and RF source and amplifier circuits 21. The MR signal (RF detector) circuits 22 are suitably interfaced with MR signal RF coils 16 located within the shielded MRI system gantry. The received MR responses are digitized by digitizer 23 and passed to processor 19 which typically includes an array processor for image processing and suitable computer program storage media (not shown) wherein programs are stored and selectively utilized so as to control the acquisition and processing of MR signal data and to produce image displays on a CRT of control terminal 24. The MRI system is provided with a control terminal 24 which may include suitable keyboard switches and the like for exerting operator control over the imaging sequence controllers, 17 and 18. Images may also be recorded directly on film or on other suitable media by printing device 25.

In conjunction with system computer/processor 19, an operator is typically presented with a menu of choices for MRI sequences and data processing techniques. In the example embodiment of this invention, one of those choices available to the operator is a program for providing an ASE sequence with a variable ΔTE for MR fluoroscopic (i.e., real-time) visualization of instruments during interventional procedures.

The Variable ASE Imaging Sequence

Figure 3:
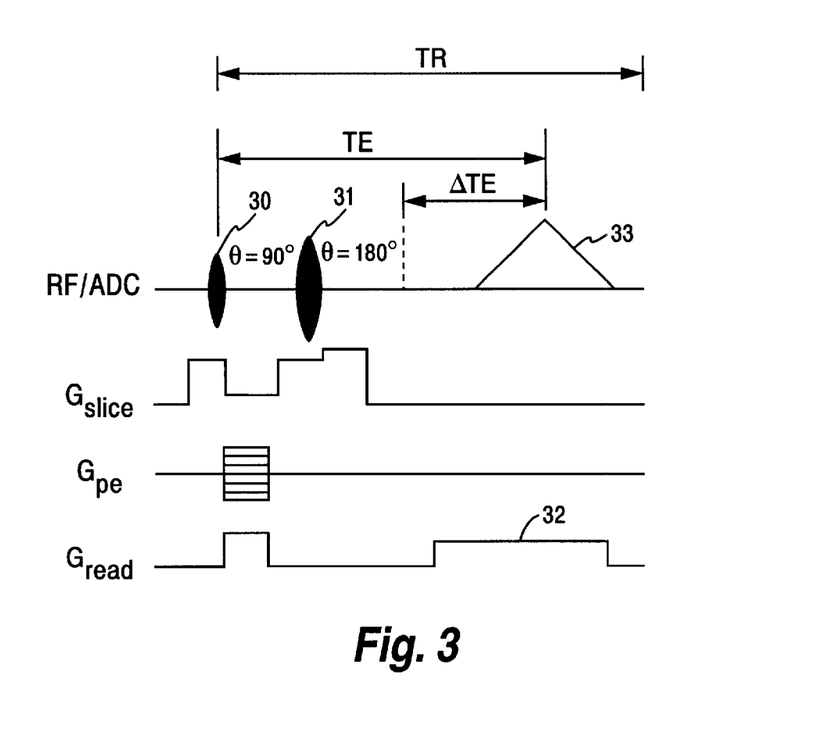
FIG. 3 is an RF and gradient waveform timing diagram of an asymmetric spin-echo imaging sequence with a variable ΔTE in accordance with the present invention.

Referring now to FIG. 3, a preferred imaging sequence of the present invention consists of an asymmetric RF pulse sequence produced by the generation of appropriately timed RF pulses, 30 and 31, slice selection gradient pulses, $G_{slice}$, and a phase encoding gradient pulse, $G_{pe}$, followed by a read-out gradient pulse 32, at $G_{read}$, which result in the acquisition of a spin-echo 33. A nuclei dephasing pulse 34 may also be applied orthogonal to the phase-encoding pulse. Essentially, each scan sequence, TR, of the present invention comprises an RF slice-selective 90° nuclei nutation ("excitation") pulse 30 followed by an RF 180° refocusing pulse 31 to generate a spin-echo. A series of scan sequences are made at differing phase-encoding gradient values to produce the image data. In a conventional spin-echo sequence the echo period, TE, between the center of excitation pulse 30 and a maximum amplitude point of resultant field-echo 33, is symmetric about RF refocusing pulse 31. In the present invention, the period, TE, may be varied by an a predetermined amount, $\Delta TE$, by adjusting the timing of refocusing pulse 31 and/or read-out gradient pulse 32. Accordingly, TE is made asymmetric about pulse 31 by an amount $\Delta TE$ and the amount of asymmetry can be controllably varied for each image produced during interventional MRI procedures to alter the clarity, contrast and size of an imaged instrument.

In another embodiment of the present invention, the amount of asymmetry is varied as a function of phase-encoding gradient steps, $G_{pe}$, such that $\Delta TE$ is different for each phase-encoding gradient value. This arrangement makes the imaging sequence sensitive to local gradients in the magnetic field but insensitive to large scale variations such as those introduced by main magnetic field inhomogeneities.

Data And Image Acquisition Steps

Figure 4:
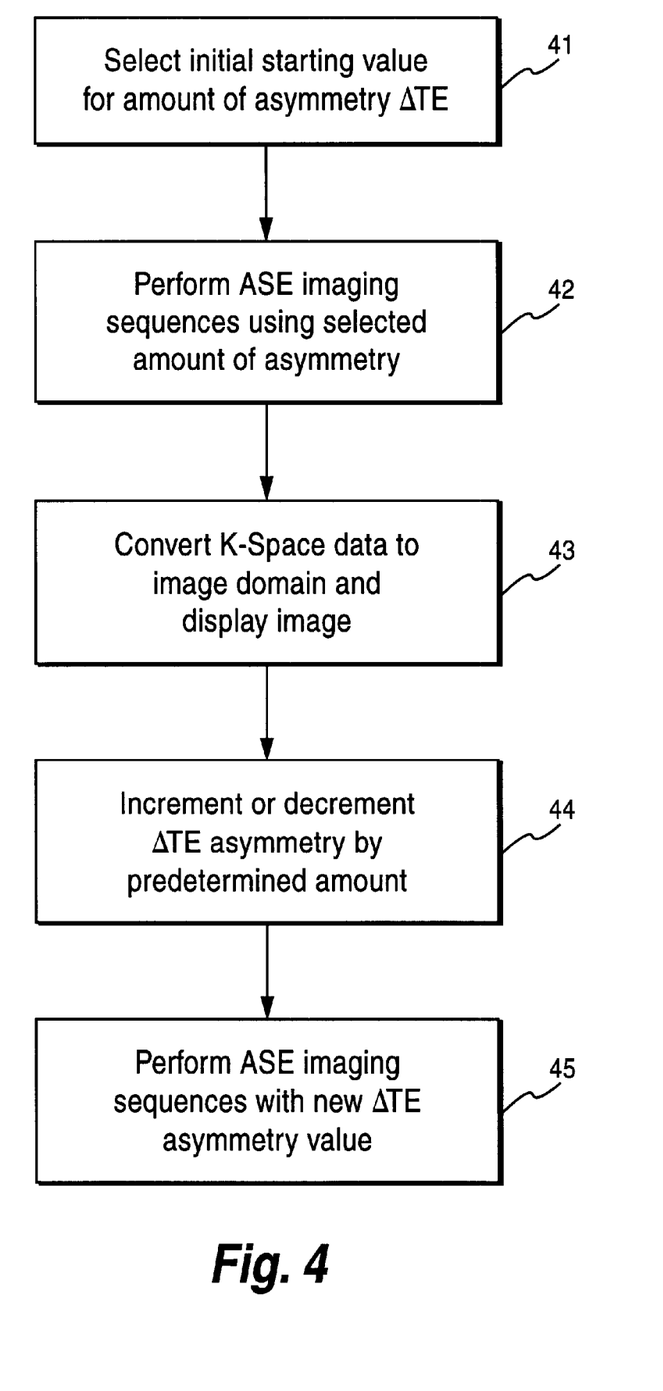
FIG. 4 is a flowchart illustrating the steps in the data processing method for an ASE imaging sequence as carried out by the MRI system of FIG. 1 in accordance with the present invention.

Referring now to FIG. 4, a flow diagram is presented that illustrates the basic steps for the imaging of paramagnetic, diamagnetic or ferromagnetic instruments within tissues during interventional procedures using an ASE sequence with variable asymmetry for controllably varying image size in accordance with the present invention. All of steps of the present invention may be implemented with a computer or processor controlled MRI system programmed using conventional programming techniques. For example, the method of the present invention may be implemented by using an appropriately programmed Toshiba OPART™ MRI system.

As indicated at step 41, an initial value for the amount of desired asymmetry, $\Delta TE$, is first selected based on an operating physician's experience or empirical trials. This starting value is input by the MRI system operator to an MRI sequence controller apparatus programmed by conventional means to provide ASE sequences with a prescribed asymmetry. Next, at step 42, ASE scanning sequences having the desired initial asymmetry are performed by the MRI apparatus during the interventional procedure. The MRI apparatus may be operated in either a single-scan or real-time "fluoro" mode. After or during acquisition of MR echo signals, the k-space data is converted to the image domain and an image is displayed, as indicated in step 43. Upon viewing the resultant image, an operator may decide to increase or decrease the apparent size of an imaged instrument by selecting an increase or a decrease in the initially selected value for $\Delta TE$. The degree of asymmetry may be automatically incremented or decremented by the system program in predetermined amounts or by a selected amount input by the system operator, as indicated at step 44. The ASE imaging sequence is then performed again using the updated value for $\Delta TE$ to generate a new image at step 45. This process may be continued as needed or desired throughout the interventional procedure.

Example Images

A 14-Gauge needle of 2 mm diameter was immersed in a gelatin-water solution and fixed by cooling to provide an example subject for the imaging method of the present invention. Example images—obtained using a Toshiba OPART™ MR scanner operated at 0.35 Tesla in accordance with the present invention—are shown in FIGS. 5A–5D. The images were generated from data acquired using the above described variable ASE sequences having a basic (fundamental) TE of 15 ms and a variable $\Delta TE$ covering a range of approximately 0–5 ms. In this example, the RF excitation and refocusing pulses each had a bandwidth of 1500 Hz and images were acquired with a TR of 500 ms, a slice thickness of 5 mm, an FOV (field of view) of 20 cm, and a pixel matrix size of 256×256 with two signal averages.

Figure 5A:
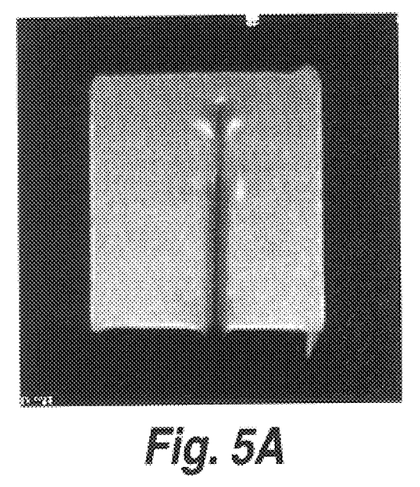
FIGS. 5(a)–5(d) comprise example asymmetric spin-echo MRI images, showing a needle immersed in gelatin, produced in accordance with the present invention.
Figure 5B:
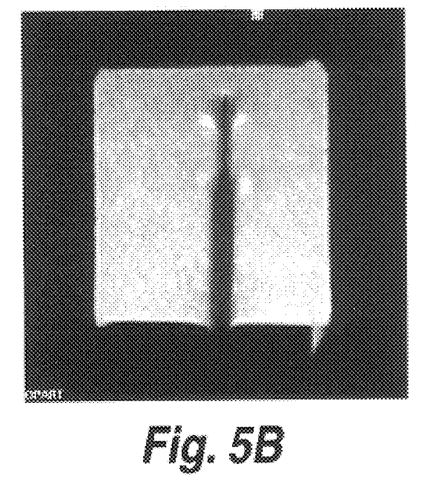
Figure 5C:
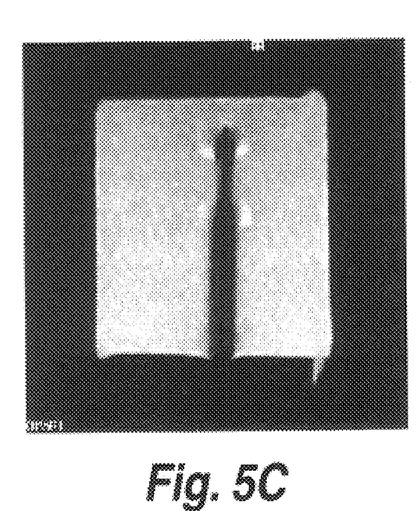
Figure 5D:
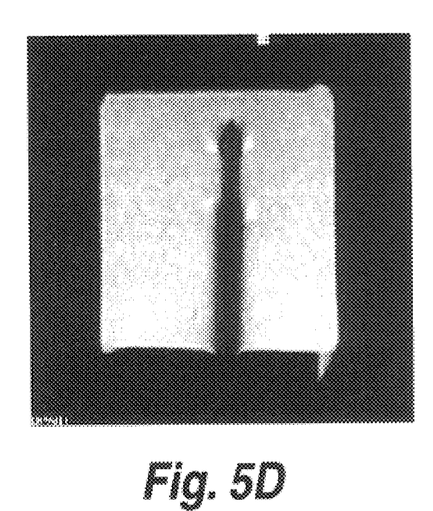

The apparent size of the imaged needle is made to vary from 2.3 mm to 9.4 mm by changing $\Delta TE$ by 1 ms for each image from 0 ms to 3 ms over a series of four images. FIG. 5A shows an ASE image having a $\Delta TE$ of 0 ms; FIG. 5B shows an ASE image having a $\Delta TE$ of 1 ms; FIG. 5C shows an ASE image having a $\Delta TE$ of 2 ms; and FIG. 5D shows an ASE image having a $\Delta TE$ of 3 ms.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for controlling a resultant image size of an imaged instrument produced by MRI during interventional procedures, comprising the steps of:

performing ASE imaging sequences using an MRI apparatus during an interventional procedure, said ASE sequences having a predetermined initial value, $\Delta TE$, representing an amount of time asymmetry in an ASE sequence;

acquiring k-space data comprising MRI echo signals resulting from the ASE sequences;

converting acquired k-space data to image domain information via appropriate Fourier transformation and using the image domain information to display an image;

updating $\Delta TE$ by incrementing or decrementing the initial value by a selected predetermined amount; and performing ASE imaging sequences using an updated value for $\Delta TE$, wherein the updated value for $\Delta TE$ results in an increase or decrease in a resultant apparent image size of an instrument used during an interventional MRI procedure.

2. The method of claim 1 wherein ASE sequences having variable degrees of asymmetry are used in a real-time mode of MRI apparatus operation to alter the apparent image size of an imaged instrument.

3. The method of claim 1, wherein an imaged instrument is composed of paramagnetic, diamagnetic or ferromagnetic materials.

4. The method of claim 1, wherein $\Delta TE$ is updated by a predetermined amount that varies as a function of a phase-encoding gradient magnitude.

5. The method of claim 1, wherein an updating of $\Delta TE$ alters a contrast quality in the resultant apparent image of an imaged instrument.

6. A magnetic resonance imaging (MRI) apparatus comprising:

magnetic field generating and detecting coils for generating an asymmetric spin-echo MRI sequence, said sequence having a variable amount of asymmetry for controlling a resultant image size of an imaged instrument;

a pulse sequence controller generating a sequence of pulses applied to the magnetic field generating and detecting coils, said pulses including:
  (i) an imaging region selection magnetic gradient producing pulse;
  (ii) a phase encoding magnetic gradient producing pulse;
  (iii) a read-out magnetic gradient producing pulse; and
  (iv) an asymmetric RF nuclei nutation pulse sequence comprising an RF excitation pulse and at least one RF refocusing pulse, said nuclei nutation pulse sequence exhibiting a variable amount of temporal asymmetry between the RF excitation pulse, the refocusing pulse and generation of the read-out gradient pulse such that a period of time between generating an RF excitation pulse and generating an RF refocusing pulse is unequal to a period of time between the refocusing pulse and a detected NMR spin-echo signal, wherein said pulse sequence controller varies the amount of asymmetry so as to effect a resultant image size of an imaged instrument.

7. A magnetic resonance imaging (MRI) apparatus as is recited in claim 6, wherein an imaged instrument is composed of paramagnetic, diamagnetic or ferromagnetic materials.

8. A magnetic resonance imaging (MRI) apparatus comprising:

magnetic field generating and detecting coils for generating an asymmetric spin-echo MRI sequence, said sequence having a variable amount of asymmetry for controlling a resultant image size of an imaged instrument;

a pulse sequence controller generating a sequence of pulses applied to the magnetic field generating and detecting coils, said pulses including:
  (i) an imaging region selection magnetic gradient producing pulse;
  (ii) a phase encoding magnetic gradient producing pulse;
  (iii) a read-out magnetic gradient producing pulse; and
  (iv) an asymmetric RF nuclei nutation pulse sequence comprising an RF excitation pulse and at least one RF refocusing pulse, said nuclei nutation pulse sequence exhibiting a variable amount of temporal asymmetry between the RF excitation pulse, the refocusing pulse and generation of the read-out gradient pulse such that a period of time between generating an RF excitation pulse and generating an RF refocusing pulse is unequal to a period of time between the refocusing pulse and a detected NMR spin-echo signal, wherein the amount of asymmetry effects a resultant image size of an imaged instrument and the amount of asymmetry is varied by the pulse sequence controller as a function of a phase-encoding gradient magnitude produced by the phase-encoding gradient pulse.

9. A magnetic resonance imaging (MRI) apparatus as is recited in claim 6, wherein the amount of asymmetry effects a contrast quality in a resultant image of an imaged instrument.

10. A magnetic resonance imaging (MRI) apparatus as is recited in claim 6, wherein the amount of asymmetry determines a resultant image size of an imaged instrument introduced into tissues for a fluoroscopic interventional MRI procedure.

11. A magnetic resonance imaging (MRI) apparatus as is recited in claim 6 wherein said pulse sequence controller generates said pulses under control of a programmable computer processor.

* * * * *

UNITED STATES PATENT AND TRADEMARK OFFICE
CERTIFICATE OF CORRECTION

PATENT NO.   : 6,332,088 B1
DATED        : December 18, 2001
INVENTOR(S)  : Zhang et al.

It is certified that error appears in the above-identified patent and that said Letters Patent is hereby corrected as shown below:

<u>Title page,</u>
Item [75], the first-named inventor's name is misspelled. It should read -- Weiguo -- (not "Weigno").

Signed and Sealed this

Tenth Day of September, 2002

Attest:

JAMES E. ROGAN
*Attesting Officer*            *Director of the United States Patent and Trademark Office*